United States Patent
Yamamoto et al.

(10) Patent No.: US 6,803,062 B2
(45) Date of Patent: Oct. 12, 2004

(54) PROCESS FOR PRODUCING HYDROLYZED PROTEIN

(75) Inventors: Ko Yamamoto, Kawasaki (JP); Junichiro Kojima, Tokyo (JP); Toshimasa Ishii, Kawasaki (JP); Inao Oyama, Kawasaki (JP); Mitsuyoshi Seki, Kawasaki (JP); Hidetsugu Nakazawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/183,686

(22) Filed: Jun. 28, 2002

(65) Prior Publication Data

US 2003/0012848 A1 Jan. 16, 2003

Related U.S. Application Data

(63) Continuation of application No. PCT/JP00/07645, filed on Oct. 30, 2000.

(51) Int. Cl.$^7$ .................................................. A23L 1/00
(52) U.S. Cl. ............................ 426/52; 426/18; 426/34; 426/42; 426/43; 426/49; 426/55; 426/56; 426/60; 426/656; 426/657
(58) Field of Search ................................ 426/7, 18, 32, 426/34, 41, 42, 43, 44, 46, 49, 52, 55, 56, 60, 656, 657

(56) References Cited

FOREIGN PATENT DOCUMENTS

| | | |
|---|---|---|
| EP | 0 072 322 | 2/1983 |
| EP | 1 074 632 A1 | 2/2001 |
| JP | 48-58157 | 8/1973 |
| JP | 48-67461 | 9/1973 |
| JP | 48-82068 | 11/1973 |
| JP | 51-35461 | 3/1976 |
| JP | 51035461 A | 3/1976 |
| JP | 63-074465 A | 4/1988 |
| JP | 63-216437 A | 9/1988 |
| JP | 6-125734 | 5/1994 |
| JP | 9-75032 | 3/1997 |
| JP | 9-121807 | 5/1997 |
| JP | 11-103834 | 4/1999 |
| JP | 11-313693 | 11/1999 |
| JP | 2000-88 | 1/2000 |
| JP | 2000-14394 | 1/2000 |
| JP | 2000-212198 | 8/2000 |
| WO | WO99/57302 | 11/1999 |

*Primary Examiner*—Leslie Wong
(74) *Attorney, Agent, or Firm*—Oblon, Spivak, McClelland, Maier & Neustadt, P.C.

(57) ABSTRACT

A hydrolyzed protein which can be used as seasonings or the like is produced by heating and maintaining an aqueous dispersion of a protein-containing starting material, while under an acidic condition, with a plate-type heat exchanger using a liquid as a heat medium to make the aqueous dispersion substantially aseptic and then subjecting the resulting aqueous dispersion with an action of a proteolytic enzyme.

19 Claims, No Drawings

PROCESS FOR PRODUCING HYDROLYZED PROTEIN

CROSS REFERENCES TO RELATED APPLICATIONS

This application is a continuation of PCT International Application No. PCT/JP00/07645, which was filed on Oct. 30, 2000, and which is incorporated herein by reference in its entirety.

BACKGROUND OF THE INVENTION

1. Field of the Invention

The present invention relates to novel processes for producing hydrolyzed protein. More specifically, the present invention relates to processes for easily producing high-quality, highly stable hydrolyzed protein useful for seasonings or the like by hydrolyzing a protein-containing starting material by an action of an enzyme. The present invention further relates to processes for preparing food products by incorporating hydrolyzed protein prepared by such a process in a food product.

2. Discussion of the Background

Various processes are already known for producing hydrolyzed protein from a protein-containing starting material by an enzyme on an industrial production scale.

For example, Japanese Patent Kokai Publication JP-A-51-35,461 discloses a process for producing a liquid seasoning by reacting denatured de-fatted soybeans with an alkaline protease and a peptidase, and Japanese Patent Kokai Publications JP-A-6-125,734, JP-A-9-75,032, and JP-A-9-121,807 disclose a process for producing a seasoning by hydrolysis of various proteins with a protease and a peptidase contained in a culture of a koji mold.

Further, a process for producing a seasoning having a high content of glutamic acid (see Japanese Patent Kokai Publication JP-A-2000-88) or an amino acid mixture with reduced browning (see Japanese Patent Kokai Publication JP-A-2000-14,394) by using a microbial culture obtained by a specific incubation method or by using a specific condition of hydrolysis of a protein-containing starting material have also been reported.

However, such conventional techniques are problematic in that during the production of a hydrolyzate by enzymatic hydrolysis of a starting material containing a solid protein, the quality and the yield of the hydrolyzed protein obtained are decreased due to the growth of microorganisms other than the microorganism used as an enzyme source, so-called contaminants, in the hydrolysis step. In order to solve this problem, bacteriostatic substances such as alcohols, sodium chloride, ethyl acetate, and the like have been employed in the hydrolysis step in the conventional processes (see the above Japanese Patent Kokai Publications JP-A-6-125,734 and JP-A-9-75,032).

However, in these processes, an additional step of separating and removing bacteriostatic substances after the hydrolysis step was required. Especially when sodium chloride was employed as a bacteriostatic substance, it was quite difficult to decrease sodium chloride to less than an appropriate concentration without deteriorating the quality of the resulting hydrolyzed protein. Moreover, it was almost impossible to prevent the occurrence of a so-called brewing odor or soy sauce odor in the hydrolyzed protein obtained by hydrolysis in the presence of bacteriostatic substances. As a result, the range of utilities of the resulting hydrolyzed protein was extremely restricted.

Further, in the conventional processes, attempts were naturally made to subject a starting material containing a solid protein to hydrolysis after removal or sterilization of contaminants incorporated in the protein-containing starting material or a microbial culture as an enzyme source. It is relatively easy to perform hydrolysis of a protein-containing starting material after sterilization thereof on a laboratory scale. However, in industrial mass-production, the prevention of microorganism contamination in the sterilization step and the hydrolysis step is very difficult to perform.

In the commercial production of a liquid seasoning of an enzymatically hydrolyzed protein, it is important to prevent microorganism contamination in view of quality control. The main contamination sources include the protein-containing starting material, the enzyme preparation or the enzyme-containing fermentation broth and the production equipment. In the step of sterilizing a protein-containing starting material prior to the enzymatic hydrolysis, bacteriostatic agents such as alcohols, sodium chloride, ethyl acetate and the like have been employed as stated above. However, incorporation of these bacteriostatic agents into products limits the use of the products. Further, the additional step of removal of such bacteriostatic agents incurs the problem of increased production cost.

With respect to the enzyme preparation or the enzyme-containing fermentation broth, a filtrate of the enzyme solution with an absolute filter or an aseptically fermented enzyme broth is appropriate for the aseptic use in the subsequent hydrolysis process. For the sterilization of the production equipment, there are treatment methods depending on characteristics of the equipment. Washing with an alkaline washing solution or an acid washing solution and steam heating are available and may be performed at a low cost.

Accordingly, the most serious problem among others is to completely sterilize a protein-containing starting material without the use of sodium chloride or alcohols. In particular, the sterilization of a protein-containing starting material containing solid matter involves a lot of difficulties as follows. Looking at a typical method, in which a pulverized protein is dispersed in water and the dispersion is heat-sterilized, it is first found that the dispersion contains solid matter, the inside of which is hardly heated by ordinary heating methods. Further, when the protein concentration in the dispersion is increased, the viscosity of the dispersion becomes quite high, and equipment having a very high power for feeding the dispersion is required, which increases the production cost. In particular, a protein-containing starting material such as wheat gluten includes active gluten which is easy to bind when its powder is dispersed in water. Thus, it cannot be evenly dispersed. Moreover, even if the dispersion can be fed smoothly, the protein ingredients are denatured and solidify inside the unit for the sterilization step, such as a plate-type heat exchanger or a nozzle-type heater, to clog the same.

As one technique to partially solve this problem, a method has been proposed in which a protein-containing starting material is finely pulverized to a diameter of not more than 300 $\mu$m and dispersed in hot water of not less than 80° C., thereby improving the dispersibility of the protein-containing starting material and preventing bubbles from being incorporated into the dispersion at the same time (see Japanese Patent Kokai Publication JP-A-11-313,693). In this method, the dispersing of the protein-containing starting material which was difficult in the past is enabled for protein dispersions having a relatively low concentration. Further, the viscosity of the dispersion is decreased, and bubbles are not incorporated into the dispersion, whereby complete sterilization is enabled in the subsequent sterilization step.

However, in order to decrease the production cost in commercial production, it is necessary to increase the concentration of the protein dispersion and to improve the equipment productivity in the subsequent hydrolysis step. None of the prior techniques are satisfactory for sterilizing such a protein dispersion having a high concentration.

That is, as the concentration of the protein dispersion is increased, the protein-containing starting material is hardly dispersed uniformly. Moreover, when the protein-containing starting material is aggregated in an aqueous medium, it contains air and the heating is not uniform so that complete sterilization is difficult in this state. Further, even though the protein-containing starting material can be dispersed, the viscosity of the dispersion is high, and accordingly, it is difficult to feed for the subsequent step. In theory, it is possible to disperse the protein-containing starting material with a high-performance dispersion vessel and feed the dispersion with a pump for a highly viscous liquid. However, such production equipment is expensive.

With respect to the sterilization step, there are two methods, a direct heating method and an indirect heating method. In the direct heating method, a heat medium and a subject (such as the dispersion of the protein-containing starting material) to be treated are directly contacted with each other to heat the subject. A direct heating-type ultra high temperature instantaneous sterilizer for high viscosity is available. According to this method, even a food having a high viscosity of several hundreds of thousands of centipoises [c.p. (mPa·s)] can be heated in a short period of time by being mixed with a steam as a heat medium at good efficiency, and completely sterilized by maintaining the temperature for a predetermined period of time. Moreover, the heated subject can be subjected to reduced pressure to evaporate the steam charged in the heating and instantaneously cooled to approximately the original temperature. Nevertheless, since the steam as the heat medium is directly mixed with the food, the use of chemicals such as boiler compounds and the like in the water supply to the boiler is limited, and it is necessary to further add a step of producing steam which is suitable for use in the food. In addition, there is the problem that the method cannot be applied to a subject which contains solid matter having a size of several millimeters.

Meanwhile, in the indirect heating method, a subject to be treated is indirectly heated with a heat medium via a heat transfer member. The indirect heating method has been often used in the sterilization of highly viscous food in the food industry because of the simple mechanical structure, good operability, and low-cost apparatus. In this connection, a tubular system or a scratch-type sterilizer is a typical indirect heating-type sterilizer for highly viscous foods. The tubular system is a system in which a highly viscous food is passed through a tube and heated from the outside with hot water or the like. Since the pressure supplied is increased owing to the pressure drop in a pipe, its length is limited, so that plural pipes are sometimes arranged in parallel to give a multi-pipe system. Advantageously, the structure is simple, and the system is easy to assemble or disassemble and is also easy to wash. On the other hand, the heat transfer surface is liable to scorch. And the fluid flowing there inside is hard to mix, and thus the temperature tends to be non-uniform. Accordingly, this method is inappropriate when strict control of temperature is required.

The scratch-type heat exchanger is designed to offset the defect of the tubular system, and scratches off the food near the heat transfer surface with a vane to prevent scorching. At the same time, the food in the tube can be stirred for thermal uniformity. However, the scorching on the heat transfer surface still cannot completely be prevented for almost all highly viscous foods.

After a fixed time of operation, the heat exchanger is usually washed in the assembled state. However, in the case of hard scorching, the heat exchanger has to be disassembled and washed. These indirect heating-type sterilizers are still problematic in the heat transfer, and sometimes cause thermal deterioration of qualities (degradation of nutrients, taste, color and the like) owing to a long heating time and mechanical change (physical change in viscosity and the like) caused by stirring.

Moreover, in the fermentation industry in which a complete sterilization step of a culture medium is indispensable, an indirect heating plate-type heat exchanger using steam as a heat medium is generally used for sterilizing a culture medium. However, when heat sterilization is conducted by simply passing a protein dispersion having a high concentration through such a heat exchanger, the protein dispersion is thermally denatured, a decrease in heat transfer efficiency and an increase in pressure drop due to scaling in the heater or the cooler occur, and in the worst case, it becomes impossible to pass the dispersion.

Thus, there remains a need for an improved method for performing the complete sterilization of a highly viscous protein dispersion having a high concentration on an industrial scale, which does not depend on a special technique or equipment.

SUMMARY OF THE INVENTION

Accordingly, it is one object of the present invention to provide novel methods for preparing hydrolyzed protein.

It is another object of the present invention to provide novel methods for sterilizing or rendering aseptic a protein-containing starting material for the production of hydrolyzed protein.

It is another object of the present invention to provide novel methods for sterilizing or rendering aseptic an aqueous dispersion of a protein-containing starting material for the production of hydrolyzed protein.

It is another object of the present invention to provide novel methods for sterilizing or rendering aseptic a highly concentrated aqueous dispersion of a protein-containing starting material for the production of hydrolyzed protein.

It is another object of the present invention to provide novel methods in which an aqueous dispersion of a protein-containing starting material, especially, a dispersion having a high concentration can easily be made substantially aseptic in the production of an enzymatically hydrolyzed protein on an industrial scale without introducing special equipment, thereby improving the equipment productivity and the product quality and widening the use range of products.

It is another object of the present invention to provide novel methods for preparing food products by adding a hydrolyzed protein so produced to a food product.

These and other objects, which will become apparent during the following detailed description, have been achieved by the inventors' discovery that an aqueous dispersion of a protein-containing starting material can be made substantially aseptic by being heated and maintained while under an acidic condition with a plate-type heat exchanger using a liquid as a heat medium. This finding has led to the completion of the present invention.

That is, a process for producing a hydrolyzed protein according to the present invention is characterized by heating and maintaining an aqueous dispersion of a protein-containing starting material while under an acidic condition with a plate-type heat exchanger using a liquid as a heat medium to make the aqueous dispersion substantially aseptic, and then subjecting the resulting aqueous dispersion to an action of a proteolytic enzyme. Thus the present invention makes it possible to mass-produce a hydrolyzed protein easily on an industrial scale.

Thus, the present invention provides a method for rendering a protein-containing starting material substantially aseptic, wherein said method comprises:

(a) heating an aqueous dispersion of a protein-containing starting material with a plate-type heat exchanger with a liquid heating medium, to obtain a heated dispersion; and (b) maintaining said heated dispersion at an elevated temperature, to obtain a substantially aseptic dispersion, wherein said aqueous dispersion is acidic during said heating and said heated dispersion is acid during said maintaining.

As the aqueous dispersion of the protein-containing starting material, a dispersion having a high concentration of preferably at least 10 g/dl, more preferably 10 to 50 g/dl or so, is used. The dispersion should be under an acidic condition at a time for the step of heating and maintaining (heating and retention steps). It is preferable that an acidic condition is employed not only in the heating and retention steps but also at the stage of preparing the dispersion. Further, with respect to the acidic condition in the heating and retention steps, the pH value is preferably between 3 and 6. Further, as the liquid heating medium used in the plate-type heat exchanger, hot water of 120 to 150° C. is preferably used. Under such conditions, the protein-containing starting material is heated to 120 to 140° C. (subject temperature, i.e., the temperature of the dispersion) and maintained at that temperature for 1 to 20 minutes or so, preferably for 5 to 15 minutes or so. Such a construction of the present invention makes it possible to prevent denaturation of the protein and perform complete sterilization of the protein-containing starting material dispersion having a high concentration.

A key feature of the present invention is that a uniform aqueous dispersion of the protein-containing starting material is heated and maintained under the foregoing specific conditions. By this characteristic, even when using a protein-containing starting material dispersion having a high concentration, the denaturation of the protein can be prevented and the dispersion can be made substantially aseptic, which leads to an improvement of the productivity and the stabilization of the quality.

Further, in the process for producing a hydrolyzed protein according to the present invention, a partially hydrolyzed protein can be used as a protein-containing starting material. The protein dispersion having a high concentration can be easily produced by previously lowering the molecular weight of the protein-containing starting material.

DETAILED DESCRIPTION OF THE PREFERRED EMBODIMENTS

As noted above, in a first embodiment, the present invention provides a method for rendering a protein-containing starting material substantially aseptic, wherein said method comprises:

(a) heating an aqueous dispersion of a protein-containing starting material with a plate-type heat exchanger with a liquid heating medium, to obtain a heated dispersion; and (b) maintaining said heated dispersion at an elevated temperature, to obtain a substantially aseptic dispersion, wherein said aqueous dispersion is acidic during said heating and said heated dispersion is acidic during said maintaining.

As the protein-containing starting material used in the process of the present invention, vegetable or animal proteins may be used. Suitable vegetable proteins include proteins derived from wheat, corn and beans, and suitable animal proteins include proteins derived from domestic animals, poultry and fishes and shellfishes. Specific examples thereof include wheat gluten, corn gluten, de-fatted soybean, isolated soybean protein, isolated potato protein, fish meal, gelatin, collagen, whey protein, casein, skim milk, meat extract, and extract of fishes and shellfishes. Further, processed products of these proteins may also be used as the protein-containing starting materials of the present invention. Especially preferable are powders obtained by partially hydrolyzing these proteins with an acid, a protease, or the like, and drying the solubilized fractions. With respect to the extent of the hydrolysis in this case, a partially hydrolyzed protein in which the amount of formol nitrogen based on the available nitrogen that is calculated by subtracting ammonia nitrogen from total nitrogen is between 0.05 and 10%, preferably between 0.1 and 1%, or so, may be employed. This is because a dispersion of such a protein having a high concentration can be easily prepared in the subsequent dispersion step.

Next, the protein-containing starting material is uniformly dispersed in an aqueous solvent (water or a solvent composed mainly of water) such that the concentration thereof is 10 g/dl or more as a solid content. In this step, the temperature of the aqueous solvent should be in such a range that denaturation of a protein does not occur. It is preferably not more than 80° C., more preferably not more than 70° C. When denaturation of a protein occurs, the viscosity of the dispersion is increased which makes it difficult to feed the dispersion. Thus, it is undesirable.

Meanwhile, for keeping equipment costs down without changing the specification of heating and retention equipment (heat transfer area of the plate) in the subsequent sterilization step, it is preferable that the temperature of this dispersion is higher. At low temperatures, denaturation does not occur, but the viscosity is high. Accordingly, the temperature range of the dispersion is preferably between 40 and 80° C., more preferably between 50 and 70° C. Further, it is advantageous, in view of efficiency of the dispersion step, that the dispersing is conducted with a stirring mixer having a high power, preferably a stirring power of not less than 0.2 kwh per kiloliter of the liquid to be treated.

In the present invention, the aqueous dispersion of the protein-containing starting material is adjusted to an acidic pH region at least during the stage of heating and maintaining the temperature. It is preferable to adjust the pH value to an acidic region during the stage of preparing the dispersion because the dispersibility is improved and the viscosity is not increased so much during the dispersing. Further, this can prevent the denaturation of the protein and the increase of the viscosity during the heat sterilization.

The optimum pH range varies with the type of the protein-containing starting material. The pH is in such a range that the increase in the viscosity of the liquid after the heat treatment is less. It is preferably not more than 6, more preferably between 3 and 6 from the aspect of preventing corrosion of equipment. For adjusting the pH value, citric acid, lactic acid, hydrochloric acid, phosphoric acid, sulfuric acid or the like is used. The pH adjuster can be selected depending on the final product quality. Further, when the protein-containing starting material per se contains an acidic substance and the dispersion is already within the preferable pH range, there is no need to add the pH adjuster.

Subsequently, the thus-obtained aqueous dispersion of the protein-containing starting material is heat-treated (heating step) with a plate-type heat exchanger. The plate is preferably a plate appropriate for a highly viscous liquid. For example, a plate called a corrugated plate or a free flow plate which has been developed for food processing only is preferably used. By using these plates, the contact point between plates is minimized, or the contact points of plates are changed to a contact line, or a gap between plates is adjusted, so that the treatment of a subject containing a solid matter as well as, beverages and seasonings with a high viscosity is enabled. Further, the temperature in the heating step is preferably between 120 and 140° C. (subject temperature, i.e., temperature of the dispersion).

The maintaining (retention) step is conducted by passing the heated protein dispersion through a retention pipe or piping connected to the plate-type heat exchanger. The retention time in the retention step is changed according to the properties of the starting material and/or the number of contaminants contained in the starting material by adjusting the diameter and the length of the retention pipe or piping. For example, when the protein-containing starting material is liable to denaturation, it is advisable that the temperature is decreased or the retention time is shortened. In the case when a large number of contaminants are present, it is advisable that the temperature is increased or the retention time is prolonged.

The heating time is preferably between 1 and 20 minutes, more preferably between 5 and 15 minutes. Moreover, the heat medium used in the heating step is preferably hot water of a high temperature. The temperature of hot water is preferably between 120 and 150° C. When steam is used instead of hot water as a heat medium, denaturation of a protein tends to occur, scales are adhered to the surface of the plate on the side of the liquid to be treated, and clogging occurs so that the passage of the dispersion is made difficult. Also in the cooling step of cooling the protein dispersion after the heating and retention steps, it is advisable to use a plate for a highly viscous liquid as in the heating step.

In the conventional technique, as stated above, sterilization of a wheat gluten emulsion is conducted using the same plate-type heat exchanger as in the present invention (see Example 2 in Japanese Patent Kokai Publication JP-A-11-313,693). This method is not problematic when the concentration of an aqueous dispersion of a protein-containing starting material is relatively low. However, for sterilizing an aqueous dispersion of the protein-containing starting material having a high concentration as used in the present invention, there remains a problem that denaturation of the protein or clogging of the plate on the side of the treating liquid occurs and sterilization is difficult. Incidentally, in this conventional technique (refer to Example 2 in Japanese Patent Kokai Publication JP-A-11-313,693), (gluten concentration, 50 g/dl) is mentioned, but (gluten concentration, 50 g/l) is correct, which is clear to a person skilled in the art from the entire description of the specification thereof.

The aqueous dispersion of the protein-containing starting material which is prepared by the heating and retention step in this manner is substantially aseptic. In the context of the present invention, the term "substantially aseptic" refers to a state in which contaminants cannot be detected from the liquid after sterilization by at least an ordinary detection method.

The aseptic protein-containing starting material may then be used to prepare a hydrolyzed protein. Thus, in a second embodiment, the present invention provides a method for producing a hydrolyzed protein, comprising:

(a) heating an aqueous dispersion of a protein-containing starting material with a plate-type heat exchanger with a liquid heating medium, to obtain a heated dispersion;

(b) maintaining said heated dispersion at an elevated temperature, to obtain a substantially aseptic dispersion; and (c) subjecting said substantially aseptic dispersion to hydrolysis with a proteolytic enzyme, wherein said aqueous dispersion is acidic during said heating and said heated dispersion is acidic during said maintaining.

In this embodiment, steps (a) and (b) may be carried out as described above.

The aqueous dispersion of the protein-containing starting material is mixed with a proteolytic enzyme preparation or a microorganism culture containing a proteolytic enzyme substantially free of microorganism contamination, and hydrolysis is performed in a hydrolysis vessel which is aseptically controlled. The term "substantially free of microorganism contamination" as used herein means "substantially free from microorganisms (contaminants) except the microorganism which produces the proteolytic enzyme." As a result, a hydrolyzed protein with desired qualities can be produced stably without undergoing contamination during the hydrolysis.

As the microorganism having a high productivity of a proteolytic enzyme, various microorganisms can be used regardless of the taxonomical position thereof. Considering that the final product is used for food, microorganisms used so far in the field of food or brewing industry are appropriate. Filamentous fungi are preferable, and a koji mold or *Bacillus subtilis* for food production is more preferable. As the koji mold, yellow-green koji molds typified by *Aspergillus oryzae* and *Aspergillus soyae* are preferable.

As these microorganisms, strains which are newly isolated from a commercial rice koji, a koji for brewing soy sauce, "natto" (fermented soybeans) or a seed culture for manufacturing "natto" and whose characteristics are identified, may be used. Further, strains of these microorganisms obtainable from a depositary are also available. In any case, it is required to confirm that contaminants are absent in the culture of the strains prior to the use. When contaminants are present, an isolated culture is prepared through single colony isolation and is used in a state substantially without microorganism contamination.

When a microorganism culture is employed as a proteolytic enzyme source for the hydrolysis step, it is usually added to a substantially aseptic dispersion of a protein-containing starting material in the form of a liquid koji and mixed. The starting material for preparing a liquid koji may be the same as, or different from, the protein-containing starting material to be hydrolyzed. However, contaminants have to be absent in the liquid koji prepared. Accordingly, special care must be taken so that contaminants are not present when the protein-containing starting material for the liquid koji is sterilized.

As a culture medium used for preparing the liquid koji, any culture medium may be used so long as the microorganisms can grow in it. Generally, the culture medium contains a carbon source, a nitrogen source, a cofactor and the like. Examples of the carbon source include glucose, maltose, fructose, sucrose, starch hydrolyzate, lactose, mannitol, and sorbose, and these are used either singly or in combination. Preferable examples of the nitrogen source include inorganic nitrogen sources such as sodium nitrate, sodium nitrite, ammonium chloride and ammonium sulfate, organic nitrogen sources such as casamino acid, polypeptone, bacto-peptone, soybean protein, isolated soybean protein, de-fatted soybean and casein, and amino acids such as sodium L-glutamate, sodium L-aspartate, L-proline, L-alanine, glycine and L-glutamine. These may be used either singly or in combination. Examples of the cofactor include magnesium sulfate 7-hydrate, disodium hydrogenphosphate, monosodium hydrogenphosphate, monopotassium hydrogenphosphate, dipotassium hydrogenphosphate, meat extract, potassium chloride and corn steep liquor. These are used as required. The ingredients of the culture medium may be added from the beginning of the incubation or properly added during the incubation.

The conditions for incubation may be ordinary conditions for aerobic incubation. The pH is between 4.5 and 9.0, preferably between 5.5 and 8.5, and the temperature is between 15 and 40° C., preferably between 25 and 35° C. Further, with respect to the stirring speed and the amount of aeration, any conditions may be used so long as an aerobic incubation atmosphere can be maintained.

Moreover, the hydrolysis can be conducted with a commercial proteolytic enzyme preparation. In this case, the enzyme preparation has to be subjected to a step of removal of microorganisms by filtration so that contaminants are not be incorporated into the reaction system.

In the hydrolysis, any reaction vessel is available. When a microorganism culture containing a proteolytic enzyme is used, it is preferable to use a vessel in which conditions such as the temperature, aeration, stirring and the like in the reaction system are fully controllable. A submerged culture fermentor-type reaction vessel is therefore selected as an appropriate reaction vessel. Further, as a preferable example, the proteolytic enzyme may be mixed with the protein dispersion at a weight ratio of 1/20 to 2/1 such that the protein concentration is in the range between 5 and 30 g/dl, and the hydrolysis is conducted at a temperature of 20 to 60° C. for a reaction time of 10 to 100 hours.

In the present invention, the hydrolyzed protein obtained by the hydrolysis is directly used widely as a seasoning material or the like. However, in many cases, it is further subjected to removal of microorganisms, decoloring and deodorization such as activated carbon treatment, and is used as a final product. Further, according to the use purpose, it is processed into condensed paste, fine flaky powder, spray-dried powder, granules or cubic blocks and is used as a final product. Since the solution of the hydrolyzed protein is substantially free from a bacteriostatic agent such as alcohols, sodium chloride, vinegar or ethyl acetate, it is quite useful for widening the use range of the product and conducting purification and processing easily and effectively.

In addition, the hydrolyzed protein of the present invention is effective for increasing a good taste ("umami") and a sweetness, imparting a dense feel, a stickiness and a mildness, enhancing a flavor, softening a salty taste or a sourness and masking a strange taste by being added to various foods (food using flour, instant foods, agricultural, animal and marine processed products, milk products, fats and oils, frozen foods, basic and composite seasonings, confectionery, beverages and so forth). Especially, it is quite effective for imparting a sweetness, a mildness and a dense feel in the presence of soy sauce, masking a strange taste of a meat product, increasing a meat flavor, increasing a flavor in the combined use of pork, chicken, beef, marine product or vegetable extracts, and increasing a spice flavor and enhancing a hot taste in the presence of a spice.

Thus, in a third embodiment, the present invention provides a method for preparing a food product, said method comprising:

(a) heating an aqueous dispersion of a protein-containing starting material with a plate-type heat exchanger with a liquid heating medium, to obtain a heated dispersion;

(b) maintaining said heated dispersion at an elevated temperature, to obtain a substantially aseptic dispersion;

(c) subjecting said substantially aseptic dispersion to hydrolysis with a proteolytic enzyme, to obtain a hydrolyzed protein; and (d) adding said hydrolyzed protein to a food to obtain said food product, wherein said aqueous dispersion is acidic during said heating and said heated dispersion is acidic during said maintaining.

In this third embodiment, steps (a), (b), and (c) may be carried out as described above. The hydrolyzed protein may be added to the food either with or without any subsequent processing after the hydrolysis, such as removal of microorganisms, decoloring, and deodorization such as activated carbon treatment. The hydrolyzed protein may be added to the food in any form such as a condensed paste, fine flaky powder, spray-dried powder, granules or cubic blocks. The hydrolyzed protein may be added to any type of food to which hydrolyzed proteins are conventionally added such as foods containing flour, instant foods, agricultural foods, animal and marine processed products, milk products, fats and oils, frozen foods, basic and composite seasonings, confectionery, beverages, snack foods, and so forth).

Other features of the invention will become apparent in the course of the following descriptions of exemplary embodiments which are given for illustration of the invention and are not intended to be limiting thereof.

EXAMPLES

Example 1

Production of Hydrolyzed Wheat Gluten and a Liquid Seasoning (1) Production of a Wheat Gluten Dispersion and Sterilization City water of 60° C. was charged into a dispersion vessel fitted with a stirrer having a high stirring power. Dry powder of wheat gluten (a rate of formol nitrogen based on available nitrogen was approximately 0.6%) partially hydrolyzed with a proteolytic enzyme was added thereto at a concentration of approximately 30 g/dl. This gluten contained citric acid. After these were stirred and mixed for 1 hour, the pH reached between 4 and 5. Further, the viscosity of the dispersion was 0.1 Pa·s, and almost unchanged.

This dispersion was subjected to continuous sterilization treatment by indirect heating with hot water of 130 to 150° C. as a heat medium and retention for 6 minutes using a plate-type heat exchanger (plate used: Free Flow Plate N40, manufactured by Izumi Food Machinery K.K.) and a retention tube under conditions that a plate internal linear speed was between 0.3 and 0.5 m/s and a heating temperature was 130° C. The continuous sterilization treatment step could be smoothly conducted and completed, and troubles such as clogging within the plate and large increase in pressure drop did not occur at all during this step. The dispersion obtained after the sterilization treatment for 6 minutes was aseptically added to an equal amount of the sterilized culture medium (pH 7.0) comprising 0.2 g/dl of glucose and 0.01 g/dl (as nitrogen) of a de-fatted soybean hydrochloric acid hydrolyzate, and the mixture was incubated with shaking at 34° C. for 48 hours. The incubated solution was observed with a microscope. The presence of microorganisms was not identified, and the complete sterilization was confirmed. After the sterilization treatment, a small amount of scales was precipitated on the surface of the plate used. However, the scales could be removed quite easily with an ordinary scale-removing agent.

(2) Preparation of a Liquid Koji Culture

A culture medium obtained by dispersing de-fatted soybean powder, ESUSAN-PUROTEN F (manufactured by AjinomotoSeiyu K.K.) to 1.5 g/dl and further adding approximately 0.5 g/dl of L-glutamate was heat-sterilized in the range between 120 and 140° C. A liquid seed culture of a koji mold, Aspergillus oryzae ATCC 11494, grown from isolated spores in an aseptic culture medium in which de-fatted soybean powder had been dispersed at a concentration of 1.5% was inoculated in the foregoing heat-sterilized culture medium in an amount of 15%. After the inoculation, the incubation was carried out with aeration and stirring at 30° C. for 48 hours to obtain a koji mold culture without microorganism contamination. The protease activity of the resulting liquid koji was approximately 300 units/ml.

(3) Hydrolysis of a Wheat Gluten Dispersion

A gluten dispersion (slurry) sterilized with a plate-type heat exchanger was introduced into a completely sterilized fermenter. The liquid koji mold culture prepared in (2), containing a proteolytic enzyme but no microorganisms except the koji mold, was added in a half volume of the wheat gluten dispersion. The enzymatic hydrolysis was performed with aeration and stirring for 72 hours with controlling the liquid temperature to 36° C.

(4) Post Treatment of Hydrolyzed Wheat Gluten

Cells contained in the resulting hydrolyzed wheat gluten were removed by filtration, and activated carbon was added for decoloring and deodorization. Further, the product was concentrated with vacuum drying and then spray-dried.

(5) Evaluation of the Spray-dried Product of Hydrolyzed Wheat Gluten

The spray-dried product of the hydrolyzed wheat gluten was almost odorless, pale-yellow uniform powder having a rich, desirable good taste ("umami"). As a result of analysis, the content of sodium chloride was not more than 10%. Further, the number of viable cells was measured using Standard Agar Medium (made by Eiken Kagaku K.K.; yeast extract 2.5 g/l, tryptone 5 g/l, glucose 1 g/l, agar 15 g/l). As a result, incorporation of microorganisms was not detected substantially. As a total evaluation, the spray-dried product of the hydrolyzed wheat gluten has preferable properties as a good taste ("umami") seasoning material and a good taste ("umami") food material suitable for various usages. Accordingly, the thus-obtained hydrolyzed product or the ingredients thereof can be used in the form of various seasonings.

Comparative Example 1

Sterilization of a Wheat Gluten Dispersion for Comparison

A wheat gluten dispersion prepared at a concentration of approximately 20 g/dl in the same manner as in (1) of Example 1 was subjected to continuous sterilization treatment by indirect heating with steam of 130 to 150° C. as a heat medium and retention for approximately 1 minute using a plate-type heat exchanger (plate used: Free Flow Plate N40, manufactured by Izumi Food Machinery K.K.) and a retention tube under conditions that a plate internal linear speed was between 0.3 and 0.5 m/s and a heating temperature was 130° C. In the continuous sterilization treatment step, clogging within the plate and large increase in pressure drop occurred in 15 minutes after the passage of the liquid, and the step could not be completed.

From the foregoing results, it is understood that rapid denaturation of the protein can be prevented by using hot water, not steam, as a heat medium.

Example 2

Production of a De-fatted Soybean Powder Dispersion and Sterilization

City water of 60° C. was charged into a dispersion vessel fitted with a stirrer having a high stirring power. De-fatted soybean powder, ESUSAN-PUROTEN F (manufactured by Ajinomoto Seiyu K.K.) was added thereto at a concentration of approximately 20 g/dl. After these were stirred and mixed for 1 hour, the pH reached between 6 and 7. Further, the viscosity of the dispersion was 0.1 Pa·s, and almost unchanged. This dispersion was adjusted to a pH of 4.5 by adding hydrochloric acid.

This dispersion was subjected to continuous sterilization treatment by indirect heating with hot water of 130 to 150° C. as a heat medium and retention for 1 minute using a plate-type heat exchanger (plate used: Free Flow Plate N40, manufactured by Izumi Food Machinery K.K.) and a retention tube under conditions that a plate internal linear speed was between 0.3 and 0.5 m/s and a heating temperature was 130° C. The continuous sterilization treatment step could be smoothly conducted and completed, and troubles such as clogging within the plate and large increase in pressure drop did not occur at all during this step. After the sterilization treatment, a small amount of scales was precipitated on the surface of the plate used. However, the scales could be removed quite easily with an ordinary scale-removing agent.

Comparative Example 2

Sterilization of a De-fatted Soybean Powder Dispersion for Comparison

A de-fatted soybean powder dispersion was prepared as in Example 2 except that the pH adjustment by adding hydrochloric acid was not conducted.

This dispersion was subjected to continuous sterilization treatment by indirect heating with hot water of 130 to 150° C. as a heat medium and retention for approximately 1 minute using a plate-type heat exchanger (plate used: Free Flow Plate N40, manufactured by Izumi Food Machinery K.K.) and a retention tube under conditions that a plate internal linear speed was between 0.3 and 0.5 m/s and a heating temperature was 130° C. In the continuous sterilization treatment step, clogging within the plate and large increase in pressure drop occurred over the course of time, and the step could not be completed.

From the foregoing results, it is understood that denaturation of the protein can be controlled by adjusting the pH of the aqueous dispersion of the protein-containing starting material to not more than 6, as compared with the pH of 6 to 7.

Effects of the Invention

As has been thus far described, in the process of the present invention, it can convert an aqueous dispersion of a protein-containing starting material to that in the substantially aseptic state without causing thermal denaturation of the protein even at a high concentration. By subjecting the dispersion to the action of a proteolytic enzyme which is substantially without microorganism contamination, a hydrolyzed protein free from a bacteriostatic agent such as sodium chloride or the like is produced easily and efficiently. Consequently, a hydrolyzed protein having a high product quality can be produced with a high equipment productivity without introducing a special equipment, and the use of the product can also be widened.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A process for producing a hydrolyzed protein, comprising:
   (a) heating an aqueous dispersion of a protein-containing starting material with a plate-type heat exchanger using heated water as a liquid heating medium, to obtain a heated dispersion;
   (b) maintaining said heated dispersion at an elevated temperature, to obtain a substantially aseptic dispersion; and
   (c) subjecting said substantially aseptic dispersion to hydrolysis with a proteolytic enzyme,
wherein said aqueous dispersion is acidic during said heating and said heated dispersion is acidic during said maintaining.

2. The process as claimed in claim 1, wherein said aqueous dispersion contains said protein-containing starting material in a concentration of at least 10 g/dl.

3. The process as claimed in claim 1, wherein said aqueous dispersion has a pH between 3 and 6 during said heating and said heated dispersion has a pH between 3 and 6 during said maintaining.

4. The process as claimed in claim 1, wherein said liquid is water having a temperature of 120 to 150° C.

5. The process as claimed in claim 1, wherein said aqueous dispersion is heated to a temperature between 120 and 140° C. and said heated dispersion is maintained at a temperature between 120 and 140° C. for 1 to 20 minutes.

6. The process as claimed in claim 1, wherein said proteolytic enzyme is substantially free of microorganism contamination.

7. The process as claimed in claim 1, wherein said protein-containing starting material comprises a partially hydrolyzed protein.

8. The process as claimed in claim 7, wherein said partially hydrolyzed protein is one hydrolyzed to such an extent that a rate of formol nitrogen based on available nitrogen is between 0.05 and 10%.

9. The process as claimed in claim 1, wherein said protein-containing starting material comprises a vegetable protein.

10. The process as claimed in claim 9, wherein said vegetable protein is a protein derived from wheat, corn, or beans.

11. The process as claimed in claim 1, wherein said protein-containing starting material comprises an animal protein.

12. The process as claimed in claim 11, wherein said animal protein is a protein derived from a domestic animal, poultry, a fish or a shellfish.

13. The process as claimed in claim 1, wherein said proteolytic enzyme is an enzyme derived from a microorganism.

14. The process as claimed in claim 13, wherein said microorganism is a koji mold.

15. The process as claimed in claim 1, comprising:
   (1) dispersing a protein-containing starting material in an aqueous medium at a concentration of at least 10 g/dl to obtain an aqueous dispersion of said protein-containing starting material;
   (2) adjusting the pH of said aqueous dispersion to between 3 and 6 when the pH of said aqueous dispersion is not between 3 and 6;
   (3) heating said aqueous dispersion with a plate-type heat exchanger using hot water as a heat medium to an elevated temperature and maintaining said dispersion at an elevated temperature, to render said aqueous dispersion substantially aseptic;
   (4) adding a proteolytic enzyme substantially free of microorganism contamination to said aqueous dispersion; and
   (5) hydrolyzing said protein-containing starting material with said proteolytic enzyme.

16. A method for preparing a food product, said method comprising:
   (a) heating an aqueous dispersion of a protein-containing starting material with a plate-type heat exchanger using heated water as a liquid heating medium, to obtain a heated dispersion;
   (b) maintaining said heated dispersion at an elevated temperature, to obtain a substantially aseptic dispersion;
   (c) subjecting said substantially aseptic dispersion to hydrolysis with a proteolytic enzyme, to obtain a hydrolyzed protein; and
   (d) adding said hydrolyzed protein to a food to obtain said food product, wherein said aqueous dispersion is acidic during said heating and said heated dispersion is acidic during said maintaining.

17. The process as claimed in claim 16, wherein said aqueous dispersion contains said protein-containing starting material in a concentration of at least 10 g/dl.

18. The process as claimed in claim 16, wherein said aqueous dispersion has a pH between 3 and 6 during said heating and said heated dispersion has a pH between 3 and 6 during said maintaining.

19. The process as claimed in claim 16, wherein said liquid is water having a temperature of 120 to 150° C.

* * * * *